US006976964B2

(12) United States Patent
Chevallet et al.

(10) Patent No.: US 6,976,964 B2
(45) Date of Patent: Dec. 20, 2005

(54) PRESSURE MEASUREMENT DEVICE COMPRISING A MOTORIZED LOAD SENSOR AND A PROCESS FOR CONTROLLING THE DEVICE

(75) Inventors: Jacques Chevallet, Sérézin du Rhône (FR); Thierry Court, Villeurbanne (FR)

(73) Assignee: Hospal International Marketing Management, Lyons (FR)

( * ) Notice: Subject to any disclaimer, the term of this patent is extended or adjusted under 35 U.S.C. 154(b) by 147 days.

(21) Appl. No.: 10/004,862

(22) Filed: Dec. 7, 2001

(65) Prior Publication Data

US 2002/0073782 A1   Jun. 20, 2002

(30) Foreign Application Priority Data

Dec. 8, 2000  (FR) .................................. 00 15972

(51) Int. Cl.[7] .............................................. A61B 5/02
(52) U.S. Cl. .................... 600/486; 600/488; 73/715
(58) Field of Search ................... 210/645, 647, 210/741, 252, 256; 604/5.01–5.04; 600/483, 600/486, 488; 73/730

(56) References Cited

U.S. PATENT DOCUMENTS

| | | | |
|---|---|---|---|
| 5,215,450 A | | 6/1993 | Tamari |
| 5,392,653 A | * | 2/1995 | Zanger et al. ................ 73/756 |
| 6,255,609 B1 | * | 7/2001 | Samuelson et al. ....... 200/83 L |
| 6,280,406 B1 | * | 8/2001 | Dolecek et al. ............ 604/4.01 |
| 6,409,696 B1 | * | 6/2002 | Toavs et al. ................ 604/6.01 |

FOREIGN PATENT DOCUMENTS

WO   WO 99/13926   3/1999

* cited by examiner

Primary Examiner—Robert L. Nasser
(74) Attorney, Agent, or Firm—Young & Thompson

(57) ABSTRACT

A device for measuring the pressure of blood, intended to engage with a section (16) for measuring the pressure of blood, which section includes a membrane (38) which is axially deformable under the effect of the blood pressure and which is designed to be mounted on a support structure (20, 22) bearing especially a load sensor (26) arranged substantially facing the membrane (38), characterized in that it includes controlled elements (58) for the relative axial displacement of the sensitive member (52) of the load sensor (26), with respect to the support structure (20, 22), so that the axial position of the sensitive member (52) can be adjusted with respect to the external face (42) of the membrane (38), especially for the purpose of carrying out an initial calibration operation. The invention also proposes a process for controlling the device.

14 Claims, 3 Drawing Sheets

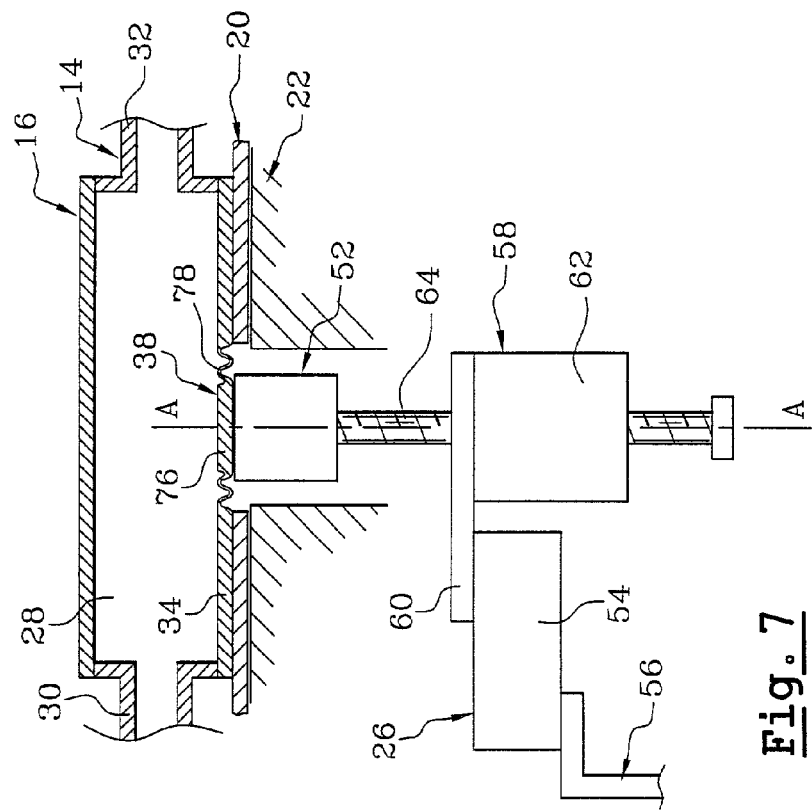
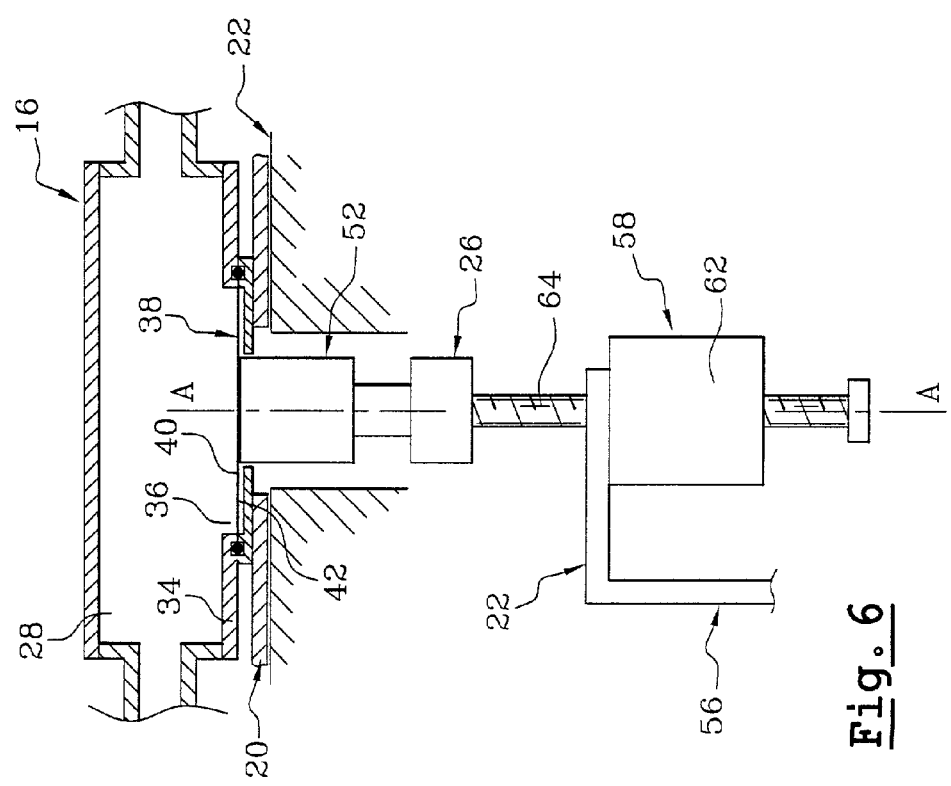

PRESSURE MEASUREMENT DEVICE COMPRISING A MOTORIZED LOAD SENSOR AND A PROCESS FOR CONTROLLING THE DEVICE

The present invention relates to a device for measuring the pressure of blood.

More particularly, the present invention relates to a device for measuring the pressure of blood, which is used in an extracorporeal blood treatment device in which the blood is taken from a patient in order to be treated and reintroduced into the body of the patient (especially for the purpose of carrying out dialysis), by means of an extracorporeal blood circuit comprising pipes and comprising at least one section for measuring the pressure of the blood flowing in a pipe.

A known type of pressure measurement section comprises, in a substantially rigid.wall, a hole which is sealed by a closure element, the internal face of which is in contact with the blood and the external face of which is in contact with the ambient air, it being possible to elastically deform or displace the closure element overall along a deformation or displacement axis which is substantially orthogonal to its general plane, under the effect of the blood pressure; the pressure measurement section is designed to be mounted onto a support structure which bears, in particular, a load sensor placed substantially facing the closure element, along the deformation axis, the load sensor being in contact, via the axial end of a sensitive member, with the external face of the closure element so as to measure the force applied axially to the internal face of the closure element by the blood pressure, in order to calculate therefrom the value of this pressure.

Generally, this type of extracorporeal blood treatment device comprises a circuit part which is formed from a casing, or cassette, of the disposable type, including pipes which are connected to the extracorporeal blood circuit.

A pressure measurement section is, for example, moulded into the cassette.

This section generally comprises a flexible membrane, which is elastically deformable along a deformation axis, and which is placed facing a load sensor.

The cassette is mounted on a support structure which comprises, for example, sensors, display means, pumping means, a control interface, an electronic control unit, etc.

The support structure comprises in particular at least one load sensor which is provided with a load transmitter which measures the forces applied by the membrane to the transmitter for the purpose of calculating therefrom the value of the blood pressure in the pressure measurement section.

The mounting of the cassette on the support structure must be sufficiently accurate so that, in the absence of pressure gradient between the two faces of the membrane, the axial end of the sensitive member of the load sensor is in contact with the external face of the membrane.

Generally, in the absence of pressure gradient between the two faces of the membrane, the load transmitter applies an initial pretensioning force $F_0$ on the external face of the membrane.

The attachment of the cassette to the support structure must therefore be very rigid, and without play, so as to avoid, during operation of the blood treatment device, relative displacements of the membrane with respect to the load transmitter, which would cause variations in the forces applied to the external face of the membrane, in particular variations of the pretensioning force $F_0$.

The pretensioning force depends on the dimensional tolerances of the cassette and of the pressure measurement section, and also on the dimensional tolerances of the load transmitter.

The aim of the invention is to remedy these drawbacks.

For this purpose, the invention proposes a device for measuring the pressure of blood, intended to engage with a section for measuring the pressure of blood flowing in a pipe, the pressure measurement section comprising, in a substantially rigid wall, a hole which is sealed by a closure element, the internal face of which is in contact with the blood and the external face of which is in contact with the ambient air, it being possible to elastically deform or displace the closure element overall along a deformation or displacement axis, which is substantially orthogonal to its general plane, under the effect of the blood pressure, the pressure measurement device comprising a load sensor secured to a support structure designed to support the pressure measurement section in such a way that the load sensor is placed substantially facing the closure element, along the deformation axis, the load sensor being designed to be in contact, via the axial end of a sensitive member, with the external face of the closure element so as to measure the force applied axially to the internal face of the closure element by the blood pressure, in order to calculate therefrom the value of this pressure, characterized in that:

- in order to operate a measurement, the load sensor co-operates with the external face of the associated closure element only by contact;
- the device comprises means for the relative axial displacement of the sensitive member, or of the measurement section, with respect to the support structure, towards the closure element;
- the device comprises a control system of the means for the axial displacement of the sensitive member, or of the measurement section, such that, during an initial adjustment phase of the axial position of the sensitive member with respect to the external face of the associated closure element, the sensitive member comes to contact with the external face of the closure element and applies a given initial pretensioning force, in order to make the pressure measurement device suitable for measurement of blood pressure greater than the ambient air pressure and for measurement of blood pressure less than the ambient air pressure.

Using the invention, it is possible to apply a given pretensioning force to the membrane.

According to other features of the invention:

- the axial displacement means comprise a device for immobilizing the sensitive member, of the respective measurement section, in a chosen axial position:
- the axial displacement means comprise a linear actuator which is capable of axially displacing the load sensor and its sensitive member;
- the extracorporeal blood treatment device comprises a load transmitter which is inserted between the closure element and the load sensor which is fixed, and the displacement of the load transmitter, which is axial with respect to the load sensor, is controlled by a linear actuator;
- the linear actuator comprises an electric motor of the stepper-motor type;
- the closure element is made in a single part with the associated rigid wall;
- the closure element is moulded with the associated rigid wall;

the device comprises a control system which controls the axial displacement means so that an initial calibration operation, which consists in choosing the axial position of the sensitive member, respectively of the measurement section, with respect to the external face of the closure element, respectively with respect to the axial end of the sensitive member, is carried out when the closure element is in its rest state, this rest state corresponding to the absence of a pressure gradient between its external face and its internal face;

the control system controls the axial displacement means so that, during the initial calibration operation, the axial displacement of the sensitive member towards the external face of the closure element, respectively the axial displacement of the measurement section towards the axial end of the sensitive member, is provoked until to obtain an initial pretensioning force which is high enough so that the pressure measurement device works in a linear region of the axial displacement means where axial play has no effect on the pressure measurements;

the control system controls the axial displacement means so that the response of the closure element to a pretensioning force can be analysed as a function of an axial displacement of the sensitive member, respectively of the measurement section;

the analysis of the response of the closure element is aimed to determine an optimum pretension force for measurements of blood pressure greater than the ambient air pressure and for measurements of blood pressure less than the ambient air pressure.

The invention also proposes a process for controlling a device for measuring the pressure of blood, intended to engage with a section for measuring the pressure of blood flowing in a pipe, the pressure measurement section comprising, in a substantially rigid wall, a hole which is sealed by a closure element, the internal face of which is in contact with the blood and the external face of which is in contact with the ambient air, it being possible to elastically deform or displace the closure element overall along a deformation or displacement axis, which is substantially orthogonal to its general plane, under the effect of the blood pressure, the pressure measurement device comprising a load sensor secured to a support structure designed to support the pressure measurement section in such a way that the load sensor is placed substantially facing the closure element, along the deformation axis, the load sensor being designed to be in contact, via the axial end of a sensitive member, with the external face of the closure element so as to measure the force applied axially to the internal face of the closure element by the blood pressure, in order to calculate therefrom the value of this pressure, characterized in that, during an initial adjustment phase of the axial position of the sensitive member with respect to the external phase of the associated closure element, the sensitive member, or the measurement section, is axially moved, with respect to the support structure, towards the closure element, respectively towards the axial end of the sensitive member, such that the sensitive member comes to contact with the external face of the closure element and applies a given initial pretensioning force, in order to make the pressure measurement device suitable for measurement of blood pressure greater than the ambient air pressure and for measurement of blood pressure less than the ambient air pressure.

According to some embodiments of the invention, the process comprises other features which are specified in the claims.

Other features and advantages of the invention will appear on reading the detailed description which follows, for the understanding of which reference can be made to the appended drawings in which:

FIG. 6 is a view similar to that of FIG. 3 which shows a first alternative embodiment of the pressure measurement system according to the invention, in which the linear actuator is capable of axially displacing the load sensor and the load transmitter;

FIG. 7 is a view similar to that of FIG. 3 which shows a second alternative embodiment of the pressure measurement system according to the invention, comprising a closure element moulded into the main wall of the pressure measurement section.

In the description which follows, identical or similar elements will be denoted by identical reference numbers.

FIG. 1 shows an extracorporeal blood treatment device 10 for the purpose of carrying out dialysis.

Figure 1:
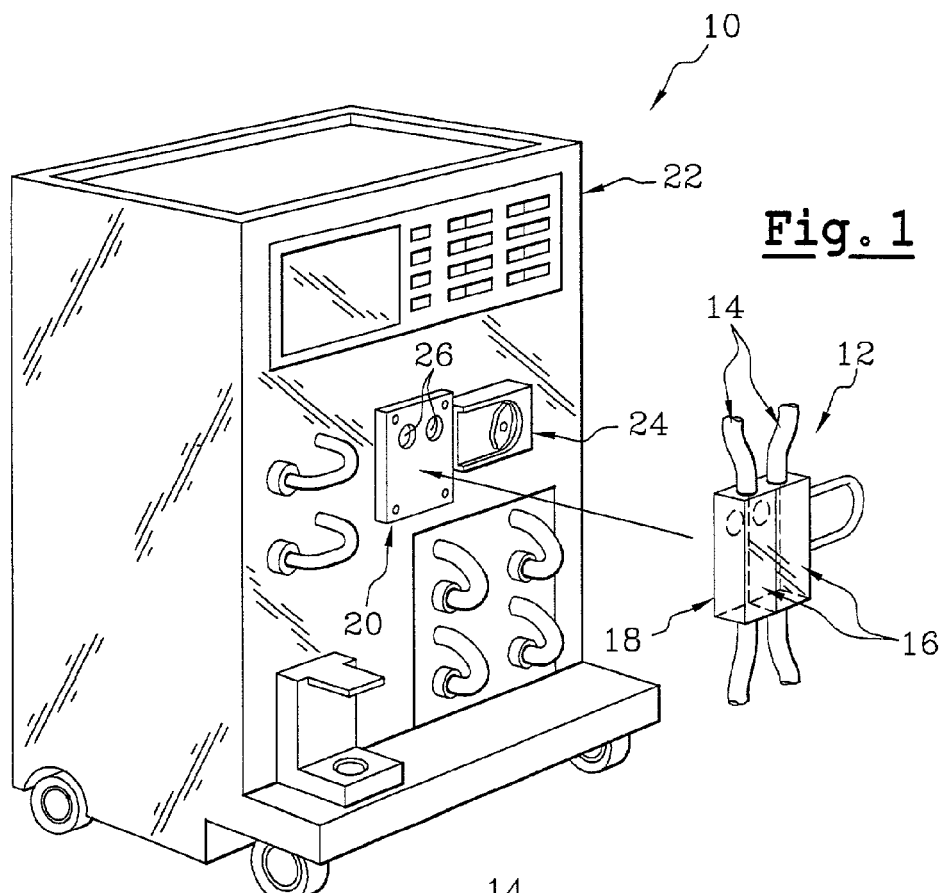
FIG. 1 is a perspective view which schematically shows an extracorporeal blood treatment device made according to the teachings of the invention.

This device 10 is designed to take blood from a patient, to treat it for the purpose of carrying out dialysis, then to reintroduce it into the body of the patient.

This device 10 comprises an extracorporeal blood circuit 12 (partially shown here) comprising pipes 14 and having at least one section 16 for measuring the pressure of blood flowing in a pipe 14.

In this case, part of the extracorporeal blood circuit 12 is made from a substantially parallelepipedal casing 18, also called cassette, which contains, in its thickness, pipes 14 for the flow of blood, which are connected to other pipes 14 of the extracorporeal blood circuit 12.

In this case, the cassette 18 comprises two similar pressure measurement sections 16 which are contained in its thickness.

The cassette 18 is designed to be mounted on a support plate 20 of a dialysis apparatus 22 which comprises, in particular, pumping means 24 to make the blood flow in the circuit 12 and means for monitoring certain parameters of the circuit 12, in particular load sensors 26 which engage with the sections 16 in order to control the pressure in the pipes 14 of the circuit 12.

The cassette 18 is, for example, moulded from polycarbonate or polypropylene, or from another suitable material.

Only a single section 16 will be described in the remainder of the description.

Figure 3:
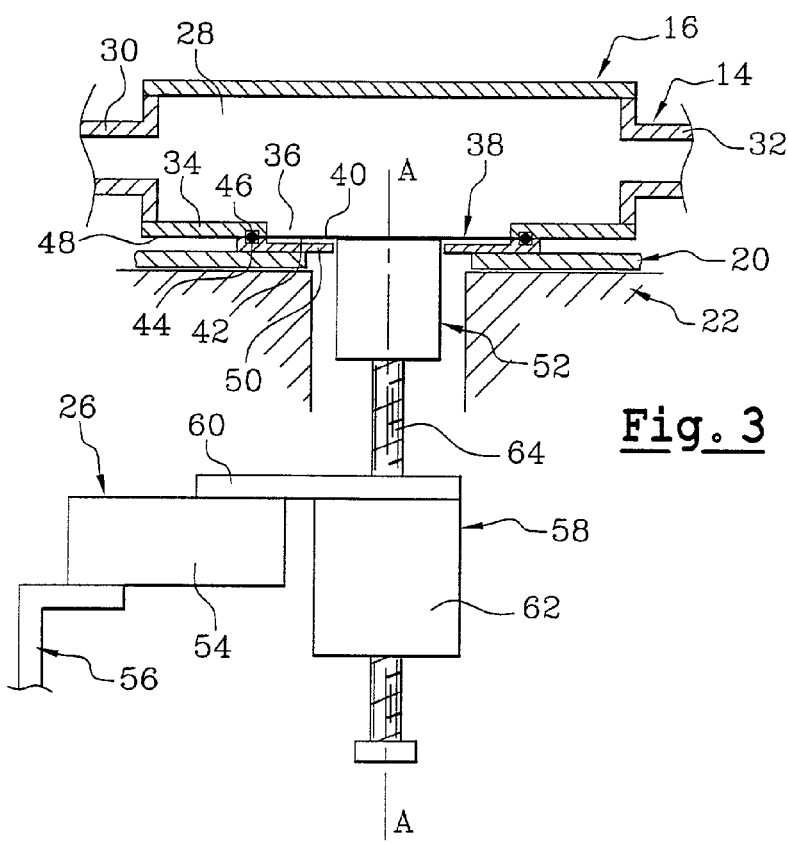
FIG. 3 is a schematic view in partial cross section which shows a pressure measurement system according to the teachings of the invention.

The pressure measurement section 16, which is shown schematically in FIG. 3, here forms a substantially parallelepipedal compartment 28 which is inserted between two branches 30, 32 of a pipe 14, and which is, for example, moulded with the cassette 18.

According to an alternative embodiment (not shown) of the pressure measurement section 16, the latter may be a module attached to the cassette 18.

A substantially rigid wall, or main wall 34, of the pressure measurement section 16 comprises a hole 36 which is sealed by a closure element 38, the internal face 40 of which is in contact with the blood and the external face 42 of which is in contact with the ambient air.

In the remainder of the description, an axial orientation along an axis A—A which is substantially orthogonal to the general plane of the main wall 34 and which passes through the centre of the hole 36 will be used.

Equally arbitrarily, an orientation from front to back along the axis A—A will be defined to correspond to an orientation from top to bottom in FIG. 3.

When the cassette 18 is mounted on its support plate 20, the main wall 34 of the pressure measurement section 16 is designed to be placed facing the support plate 20 so that the closure element 38 is facing a load sensor 26 which is mounted in the apparatus 22.

Figure 2:
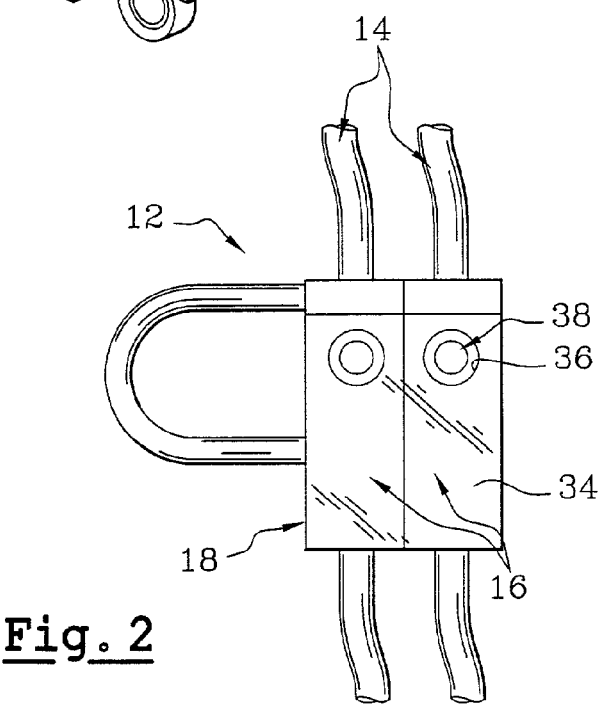
FIG. 2 is a side view which schematically shows the cassette of the device of the preceding figure.

FIG. 2 shows the cassette 18, seen from the side of the main wall 34.

In this case, the closure element 38 is a substantially disc-shaped flexible membrane.

In FIG. 3, the membrane 38 comprises a peripheral torus-shaped bead 44 for its assembly in a complementary annular groove 46 which is made in the external face 48 of the main wall 34, in the vicinity of the hole 36.

A retaining ring 50 is fixed, for example by adhesive bonding, on the external face 48 of the main wall 34, over the torus-shaped bead 44, so that the main membrane 38 is held in place axially.

The whole membrane 38 is capable of being elastically deformed along a deformation axis A—A which is substantially orthogonal to its general plane, under the effect of the blood pressure.

When the membrane 38 is in its rest state, i.e. when it is not deformed, the blood pressure being substantially equal to the pressure of the ambient air, the central part of its external face 42 is designed to be in contact with a load transmitter 52 which forms the sensitive member of a load sensor 26.

The load sensor 26 thus measures the force applied axially to the internal face 40 of the membrane 38 by the blood pressure, in order to calculate therefrom the value of this pressure.

In accordance with the teachings of the invention, the extracorporeal blood treatment device 10 comprises controlled means for the relative axial displacement of the load transmitter 52 with respect to the support plate 20 of the apparatus 22.

The means 58 for the axial displacement are controlled by a control system according to a process which will be described below.

FIG. 3 shows a load sensor 26 of the flexing beam type 54 which is fixed by one end to a support lug 56 and which comprises, at its opposite end, a linear actuator 58.

The support lug 56 is fixed with respect to the support plate 20 of the apparatus 22.

The linear actuator 58, which is inserted between the load sensor 26 and the load transmitter 52, comprises an attachment plate 60 at the end associated with the flexing beam 54.

The linear actuator 58 comprises an electric motor 62 and a threaded shaft 64 whose axis is substantially coincident with the deformation axis A—A of the membrane 38.

The load transmitter 52 is fixed to one axial end of the threaded shaft 64.

Figure 4:
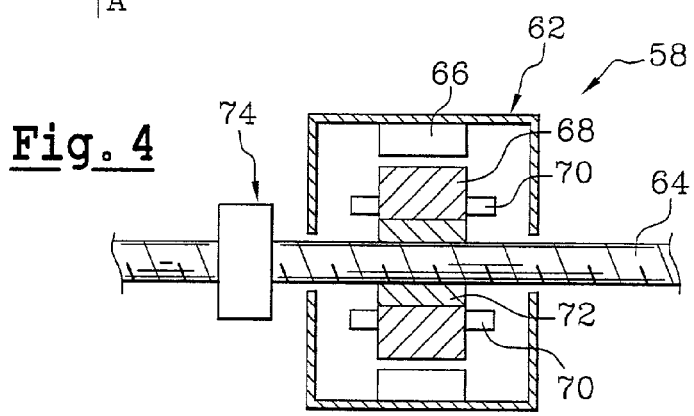
FIG. 4 is a schematic view in axial section which shows the structure of the linear actuator of the pressure measurement system of the preceding figure.

FIG. 4 shows schematically the structure of the linear actuator 58.

The electric motor 62 comprises a stator 66 which, when it is supplied with electrical current, causes the rotation of the rotor 68 of the motor 62 on the bearings 70. The rotor 68 is coaxial with the axis A—A.

The rotor 68 is rotationally secured to a nut 72 and the assembly is immobile in axial translation, such that, when the rotor 68 turns, it causes the forward or backward axial displacement of the threaded shaft 64.

For example, a linear actuator 58 which causes axial displacements in steps of twenty-one or forty-two micrometers can be used.

Advantageously, the linear actuator 58 is controlled as follows.

Before mounting the cassette 18 provided with the pressure measurement section 16, the load transmitter 52 is axially displaced backwards, in order to prevent accidental overloading of the load sensor 26 while the cassette 18 is mounted.

When the cassette 18 is fixed on its support plate 20, the load transmitter 52 is therefore not in contact with the external face 42 of the membrane 38.

An initial calibration of the membrane 38 is then carried out by axially displacing the load transmitter 52 forwards, i.e. towards the top with respect to FIG. 3, until it is in contact with a flexible portion of the external face 42 of the membrane 38 and until it a applies a given initial pretensioning force $F_0$.

When the load transmitter 52 applies a given initial pretensioning force $F_0$, the membrane 38 is slightly deformed, along the deformation axis A—A, towards the top with respect to FIG. 3.

As soon as the load transmitter 52 occupies the chosen axial position, the rotation of the motor 62 is stopped.

In the case of a motor 62 of the stepper-motor type, it is enough to supply the motor 62 to the holding position in order to axially immobilize the load transmitter 52.

If the motor 62 is not of the stepper-motor type, it is necessary to provide an axial immobilization device 74 which locks the threaded shaft 64 in the chosen axial position.

The axial immobilization device 74 is, for example, a device which rotationally locks the threaded shaft 64, in order to guarantee that the chosen axial position does not vary during the pressure measurements, especially as a function of the forces applied to the load transmitter 52.

It should be noted that the initial calibration operation is carried out when the membrane 38 is in its rest state, i.e. in the absence of a pressure gradient between its external face 42 and its internal face 40.

Generally, a calibration operation for a physical device consists in setting the device in a given state and considering the positions of the various elements as their positions of reference. In the present case, the initial calibration consists in establishing a correlation between a given pretensioning force $F_0$ and the rest state of the closure element 38.

By design, the linear actuator 58 has axial mechanical clearances, even if it is designed to carry out very precise axial positioning.

These mechanical clearances of the linear actuator 58 are due in particular to play between the rotor 68 of the electric motor 62 and its bearings 70, and to play between the threads of the nut 72 and the threads of the threaded shaft 64.

Provided the threaded shaft 64 is continuously moved in the same direction and provided an axial force is continually applied, either forwards or backwards, to the threaded shaft 64, then all the parts contributing to the axial play are providing axial pressure from the same side, and the axial play therefore has no effect on the pressure measurements.

Figure 5:
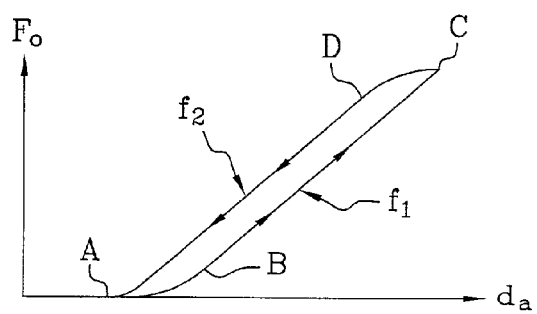
FIG. 5 is a diagram which illustrates the value of the force measured by the load sensor of the pressure measurement system of FIG. 3 as a function of the forward and backward axial displacement of the associated load transmitter.

There is therefore a mechanical backlash phenomenon which is demonstrated in the diagram of FIG. 5, which shows, at constant pressure, the pretensioning force $F_0$ measured by the load sensor 26 as a function of the forward and backward axial displacement $d_a$ of the load transmitter 52, and therefore of the threaded shaft 64.

The upward curve $f_1$ corresponds to a forward axial displacement $d_a$ of the load transmitter 52, i.e. a displacement towards the membrane 38, and therefore to an increase in the pretensioning force $F_0$ measured by the load sensor 26.

This curve $f_1$ has a first portion which is non-linear between the points A and B, and a second portion which is substantially linear between the points B and C.

The non-linear portion of the curve $f_1$ can be explained by the presence of axial play, some parts not yet providing forward axial pressure.

From the point B, the curve $f_1$ is substantially linear since all the parts contributing to the axial play are providing forward axial pressure.

The same characteristics can be observed on the downward curve $f_2$ which corresponds to a backward axial displacement $d_a$ of the load transmitter 52, and therefore to a reduction of the pretensioning force $F_0$ measured by the load sensor 26.

The non-linear portion of the curve $f_2$ is located at the beginning of the descent, between the points C and D, then the curve $f_2$ is substantially linear up to the point A.

It is therefore necessary to have, during the positioning of the load transmitter 52 with respect to the membrane 38 for the purpose of carrying out pressure measurements, an initial pretensioning force $F_0$ which is high enough so that the pressure measurement device works in the linear region of the linear actuator 58, i.e. in the region where axial play has no effect on the pressure measurements.

For the same reason, when it is desired to carry out a new initial calibration, for example if the first has not taken place correctly, it is necessary to drive the axial displacement of the load transmitter 52 to its original position, i.e. to an axial position in which no pretensioning force is applied to the membrane 38.

Advantageously, before the definitive axial positioning of the load transmitter 52 for measurement, the response of the membrane 38 to a pretensioning force $F_0$ is analysed as a function of an axial displacement $d_a$ of the load transmitter 52, and a diagram similar to that of FIG. 5 is obtained.

This analysis of the response of the membrane 38 makes it possible to obtain information which is very relevant to the mechanical characteristics of the membrane 38 before it is used for pressure measurements.

In particular, this information may be used for the purpose of identifying a fault in the membrane 38, for example an insufficient axial thickness, or for the purpose of determining an optimum pretension force $F_0$ for measurements of blood pressure greater than the ambient air pressure, called "positive" pressures, and for measurements of blood pressure less than the ambient air pressure, called "negative" pressures.

According to a first alternative embodiment of the invention, which is shown in FIG. 6, a pressure measurement system can be produced in which the linear actuator 58 is attached to a support lug 56 of the apparatus 22, and in which the load sensor 26 is attached to the front axial end of the threaded shaft 64, with its load transmitter 52.

When the linear actuator 58 is controlled, the axial displacements of the load sensor 26, with the load transmitter 52, are then controlled.

The operation of this alternative is similar to the operation of the embodiment which is shown in FIG. 3.

A second alternative embodiment of the invention is shown in FIG. 7, in which the closure element 38 of the hole 36 is made as a single part with the main wall 34, for example by moulding.

In this case, the closure element 38 has a disc-shaped, substantially rigid central pellet 76 which is delimited by a thinned peripheral annular region 78 which has an axial thickness less than the axial thickness of the main wall 34, so as to form an elastically deformable region.

Thus, by the effect of the blood pressure in the compartment 28, and by virtue of the elastic deformation of the thinned region 78, the entire central pellet 76 is capable of being displaced along a displacement axis which is substantially orthogonal to the general plane of the pellet 76 and which corresponds to the deformation axis A—A of the membrane 38 of the embodiment shown in FIG. 3.

The linear actuator 58, the load sensor 26 and the load transmitter 52 are, in this case, arranged in a manner similar to the arrangement of the embodiment shown in FIG. 3.

The operation of this alternative is similar to the operation of the embodiment which is shown in FIG. 3.

Note that the use of controlled means for displacing the load transmitter 52 axially with respect to the support plate 20 is particularly advantageous in the case of a closure element 38 which is made in a single part with the rigid wall 34, as in the second alternative embodiment which is shown in FIG. 7.

This is because, since the axial displacements of the central pellet 76 are much smaller than those of the flexible membranes, the dimensional tolerances are more exacting.

For flexible membranes, the admissible dimensional tolerances are about 0.2 to 0.3 millimeters, while for central pellets 76, the admissible dimensional tolerances are of the order of a few micrometers.

However, techniques for moulding the cassette 18, in particular where the closure element 38 is not injected directly into the cassette 18 but where it is made in the form of an attached part which is welded into the cassette 18, do not allow dimensional tolerances of the order of a few micrometers to be guaranteed.

By virtue of the invention, it is possible to accurately position the load transmitter 52 with respect to the cassette 18 and to the central pellet 76, which makes it possible to compensate for the variations in dimensions due to manufacturing tolerances of the cassettes 18 and therefore to guarantee accurate pressure measurements in all cases.

In the embodiments which have been described above, the principle of displacing the load transmitter 52 axially with respect to the support plate 20 and therefore with respect to the cassette 18 has been used.

According to an alternative embodiment (not shown) of the invention, which corresponds to a mechanical reversal of this principle, the cassette 18 is displaced axially with respect to the support plate 20, or the support plate 20, fitted with the cassette 18, is displaced axially with respect to the apparatus 22, so as to position the external face 42 of the closure element 38 axially with respect to the load transmitter 52 which is fixed.

What is claimed is:

1. Device for measuring the pressure of blood, intended to engage with a section (16) for measuring the pressure of blood flowing in a pipe (14), the pressure measurement section (16) comprising, in a substantially rigid wall (34), a hole (36) which is sealed by a flexible closure element (38), the internal face (40) of which is in contact with the blood and the external face (42) of which is in contact with the ambient air, it being possible to elastically deform or displace the closure element (38) overall along a deformation or displacement axis (A—A), which is substantially orthogonal to its general plane, under the effect of the blood pressure, the pressure measurement device comprising a load sensor (26) secured to a support structure (20, 22) designed to support the pressure measurement section (16) in such a way that the load sensor (26) is placed substantially facing the closure element (38), along the deformation axis (A—A), the load sensor (26) being designed to be in contact, via the axial end of a sensitive member (52), with the external face (42) of the closure element (38) so as to measure the force applied axially to the internal face (40) of the closure element (38) by the blood pressure, in order to calculate therefrom the value of this pressure, characterized in that:

in order to operate a measurement, the load sensor (26) co-operates with the external face (42) of the associated closure element (38) only by direct contact of the sensitive member (52) with a flexible portion of said external face (42), said sensitive member (52) and said external face being free to come into and out of contact with each other;

the device (10) comprises means (58) for the relative axial displacement of the sensitive member (52), or of the measurement section (16), with respect to the support structure (20, 22), towards the closure element (38);

the device (10) comprises a control system of the means (58) for the axial displacement of the sensitive member (52), or of the measurement section (16), such that, during an initial adjustment phase of the axial position of the sensitive member (52) with respect to the external face (42) of the associated closure element (38), the sensitive member (52) comes to contact with a flexible portion of the external face (42) of the closure element (38) and applies a given initial pretensioning force ($F_0$), in order to make the pressure measurement device (10) suitable for measurement of blood pressure greater than the ambient air pressure and for measurement of blood pressure less than the ambient air pressure;

characterized in that the control system controls the axial displacement means (58) so that, during the initial calibration operation, the axial displacement of the sensitive member (52) towards the external face (42) of the closure element (38) or the axial displacement of the measurement section (16) towards the axial end of the sensitive member (52), is provoked until an initial pretensioning force ($F_0$) is obtained which is high enough so that the pressure measurement device (10) works in a linear region of the axial displacement means (58) where axial play has no effect on the pressure measurements.

2. Device (10) according to claim 1, characterized in that the axial displacement means (58) comprise a device (74) for immobilizing the sensitive member (52), of the measurement section (16), in a chosen axial position.

3. Device (10) according to claim 1, characterized in that the axial displacement means (58) comprise a linear actuator (58) which is capable of axially displacing the load sensor (26) and its sensitive member (52).

4. Device (10) according to claim 3, characterized in that the linear actuator (58) comprises an electric motor (62) of the stepper-motor type.

5. Device (10) according to claim 1, characterized in that said sensitive member comprises a load transmitter which is inserted between the closure element (38) and the load sensor (26) which is fixed, and in that the displacement of the load transmitter, which is axial with respect to the load sensor (26), is controlled by a linear actuator (58).

6. Device (10) according to claim 1, characterized in that the closure element (38) is made in a single part with the associated rigid wall (34).

7. Device (10) according to claim 1, characterized in that the closure element (38) is moulded with the associated rigid wall (34).

8. Device (10) according to claim 1, characterized in that it comprises a control system which controls the axial displacement means (58) so that the response of the closure element (38) to a pretensioning force ($F_0$) can be analysed as a function of an axial displacement of the sensitive member (52) or of the measurement section (16).

9. Device (10) according to claim 8, characterized in that the analysis of the response of the closure element (38) is aimed to determine an optimum pretensioning force ($F_0$) for measurements of blood pressure greater than the ambient air pressure and for measurements of blood pressure less than the ambient air pressure.

10. Process for controlling a device (10) for measuring the pressure of blood, intended to engage with a section (16) for measuring the pressure of blood flowing in a pipe (14), the pressure measurement section (16) comprising, in a substantially rigid wall (34), a hole (36) which is sealed by a flexible closure element (38), the internal face (40) of which is in contact with the blood and the external face (42) of which is in contact with the ambient air, it being possible to elastically deform or displace the closure element (38) overall along a deformation or displacement axis (A—A), which is substantially orthogonal to its general plane, under the effect of the blood pressure, the pressure measurement device comprising a load sensor (26) secured to a support structure (20, 22) designed to support the pressure measurement section (16) in such a way that the load sensor (26) is placed substantially facing the closure element (38), along the deformation axis (A—A), the load sensor (26) being designed to be in contact, via the axial end of a sensitive member (52), with the external face (42) of the closure element (38) so as to measure the force applied axially to the internal face (40) of the closure element (38) by the blood pressure, in order to calculate therefrom the value of this pressure, characterized in that, during an initial adjustment phase of the axial position of the sensitive member (52) with respect to the external face (42) of the associated closure element (38), the sensitive member (52), or the measurement section (16), is axially moved, with respect to the support structure (20, 22), towards the closure element (38) or towards the axial end of the sensitive member (52), such that the sensitive member (52) comes, from out of contact, into contact with a flexible portion of the external face (42) of the closure element (38) and applies a given initial pretensioning force ($F_0$), in order to make the pressure measurement device (10) suitable to measurement of blood pressure greater than the ambient air pressure and to measurement of blood pressure less than the ambient air pressure;

characterized in that, during the initial calibration operation, the sensitive member (52) or the measurement section (16), is axially moved towards the external face (42) of the closure element (38) or towards the axial end of the sensitive member (52), until the sensitive member (52) applies an initial pretensioning force ($F_0$) which is high enough so that the pressure measurement device (10) works in a linear region of the axial displacement means (58) where axial play has no effect on the pressure measurements.

11. Process according to claim 10, characterized in that the initial adjustment phase comprises an initial calibration operation, and that, during the initial calibration operation, the sensitive member (52) or the measurement section (16), is axially moved towards the external face (42) of the associated closure element (38) or towards the axial end of the associated sensitive member (52), up to a given axial position of reference in which the sensitive member (52) is in contact with the external face (42) of the closure element (38), to establish a correlation between a given pretensioning force ($F_O$) and the rest state of the closure element (38), this rest state corresponding to an absence of a pressure gradient between its external face (42) and its internal face (40).

12. Process according to claim 10, characterized in that the initial adjustment phase comprises an analysis phase, and that the analysis phase consists in analysing the response of the closure element (38) to a pretensioning force ($F_O$) varying as a function of an axial displacement of the sensitive member (52) or of the measurement section (16).

13. Process according to claim 12, characterized in that the analysis phase is used for the purpose of identifying a fault in the structure of the closure element (38).

14. Process according to claim 12, characterized in that the analysis phase is used for the purpose of determining an optimum pretensioning force ($F_O$) for measurements of blood pressure greater than the ambient air pressure and for measurements of blood pressure less than the ambient air pressure.

* * * * *